(12) United States Patent
Weissman

(10) Patent No.: US 9,345,559 B2
(45) Date of Patent: May 24, 2016

(54) STABILIZER FOR A DENTAL IMPLANT SYSTEM AND DENTAL IMPLANT SYSTEM

(75) Inventor: Bernard Weissman, New York, NY (US)

(73) Assignee: DENTATUS USA, LTD., New York, NY (US)

( * ) Notice: Subject to any disclaimer, the term of this patent is extended or adjusted under 35 U.S.C. 154(b) by 185 days.

(21) Appl. No.: 13/992,442

(22) PCT Filed: Dec. 9, 2011

(86) PCT No.: PCT/US2011/064209
§ 371 (c)(1),
(2), (4) Date: Jun. 7, 2013

(87) PCT Pub. No.: WO2012/079007
PCT Pub. Date: Jun. 14, 2012

(65) Prior Publication Data
US 2013/0266911 A1 Oct. 10, 2013

Related U.S. Application Data

(60) Provisional application No. 61/421,393, filed on Dec. 9, 2010.

(51) Int. Cl.
*A61C 8/00* (2006.01)
*A61B 17/17* (2006.01)
(Continued)

(52) U.S. Cl.
CPC ........... *A61C 8/0009* (2013.01); *A61B 17/1673* (2013.01); *A61B 17/176* (2013.01);
(Continued)

(58) Field of Classification Search
CPC ...... A61C 8/001; A61C 1/084; A61C 8/0009; A61B 17/7241; A61B 17/1673; A61B 17/176
USPC .......... 433/72, 75, 165, 173, 174, 176, 201.1, 433/225; 606/96
See application file for complete search history.

(56) References Cited

U.S. PATENT DOCUMENTS

| 4,187,609 A | 2/1980 | Edelman |
| 4,799,886 A | 1/1989 | Wimmer |

(Continued)

FOREIGN PATENT DOCUMENTS

| FR | 2863477 | * | 6/2005 | ............. A61C 8/001 |
| WO | WO 2006038209 A2 | * | 4/2006 | ............... A61C 8/00 |

(Continued)

OTHER PUBLICATIONS

Machine translation of FR 2863477.*
(Continued)

*Primary Examiner* — Ralph Lewis
(74) *Attorney, Agent, or Firm* — Katten Muchin Rosenman LLP

(57) ABSTRACT

An implant system includes an implant and a stabilizer, which includes a manipulation portion for handling and locating the stabilizer, a main body comprising a manipulation channel, and a transverse channel for connecting the stabilizer and an implant, the transverse channel having an axis perpendicular to an axis of the manipulation channel. The implant includes a thread and the transverse channel includes threads for engaging the threads. The system further includes a jig fixture having a first arm and a second arm responsive to a manipulator; the first arm engages the manipulation portion, the second arm for engages the manipulation channel.

21 Claims, 9 Drawing Sheets

(51) Int. Cl.
  *A61C 1/08*   (2006.01)
  *A61B 17/16*   (2006.01)
  *A61B 17/68*   (2006.01)

(52) U.S. Cl.
  CPC ............... *A61C 1/084* (2013.01); *A61C 8/001* (2013.01); *A61C 8/0089* (2013.01); *A61B 17/1615* (2013.01); *A61B 17/686* (2013.01)

(56) References Cited

U.S. PATENT DOCUMENTS

| | | | | |
|---|---|---|---|---|
| 4,875,475 | A | * | 10/1989 | Comte et al. ............... 606/64 |
| 5,201,736 | A | * | 4/1993 | Strauss ........................ 606/285 |
| 5,326,263 | A | | 7/1994 | Weissman |
| 5,513,989 | A | * | 5/1996 | Crisio ............................ 433/176 |
| 5,542,847 | A | | 8/1996 | Margulies |
| 2002/0031747 | A1 | | 3/2002 | Laster et al. |
| 2006/0009771 | A1 | * | 1/2006 | Orbay et al. ................... 606/69 |
| 2006/0154205 | A1 | * | 7/2006 | Reggie ........................... 433/173 |
| 2008/0154304 | A1 | * | 6/2008 | Crawford et al. ............. 606/246 |
| 2008/0294164 | A1 | * | 11/2008 | Frank et al. ..................... 606/64 |
| 2009/0170054 | A1 | * | 7/2009 | Spahn ............................ 433/173 |
| 2010/0004698 | A1 | * | 1/2010 | De Moyer ................... 606/86 R |

FOREIGN PATENT DOCUMENTS

| | | | |
|---|---|---|---|
| WO | WO 2007122178 A2 * | 11/2007 | ............. A61B 5/103 |
| WO | WO 2008006802 A1 * | 1/2008 | ................ A61C 1/08 |

OTHER PUBLICATIONS

International Preliminary Report on Patentability and Written Opinion of the International Searching Authority dated Jun. 20, 2013, from corresponding International Application No. PCT/US2011/064209.

International Search Report and Written Opinion, dated Jul. 30, 2012, from the corresponding PCT/US2011/064209.

* cited by examiner

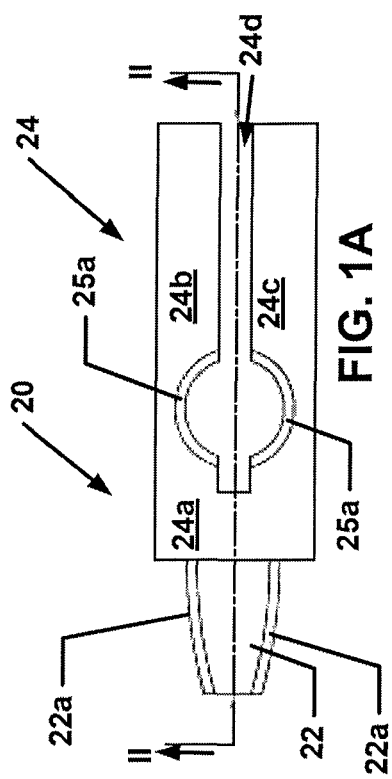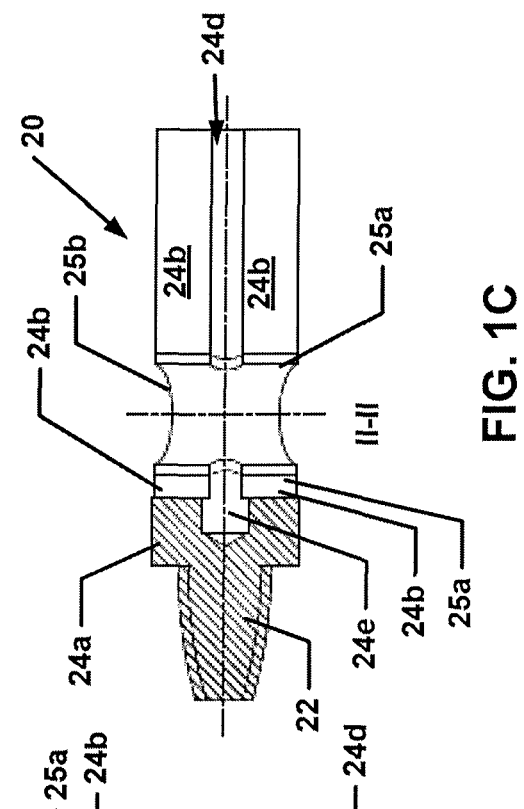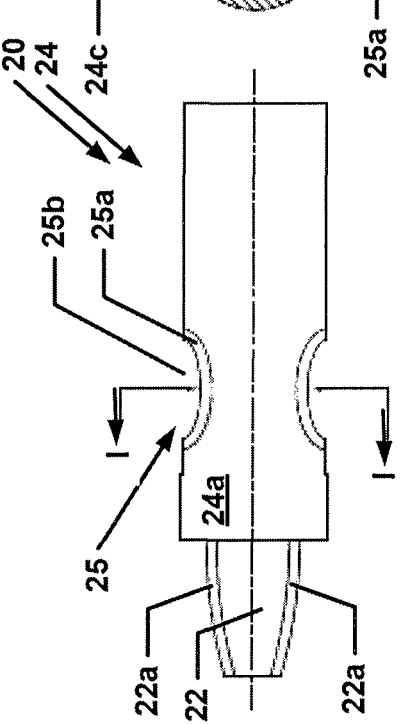

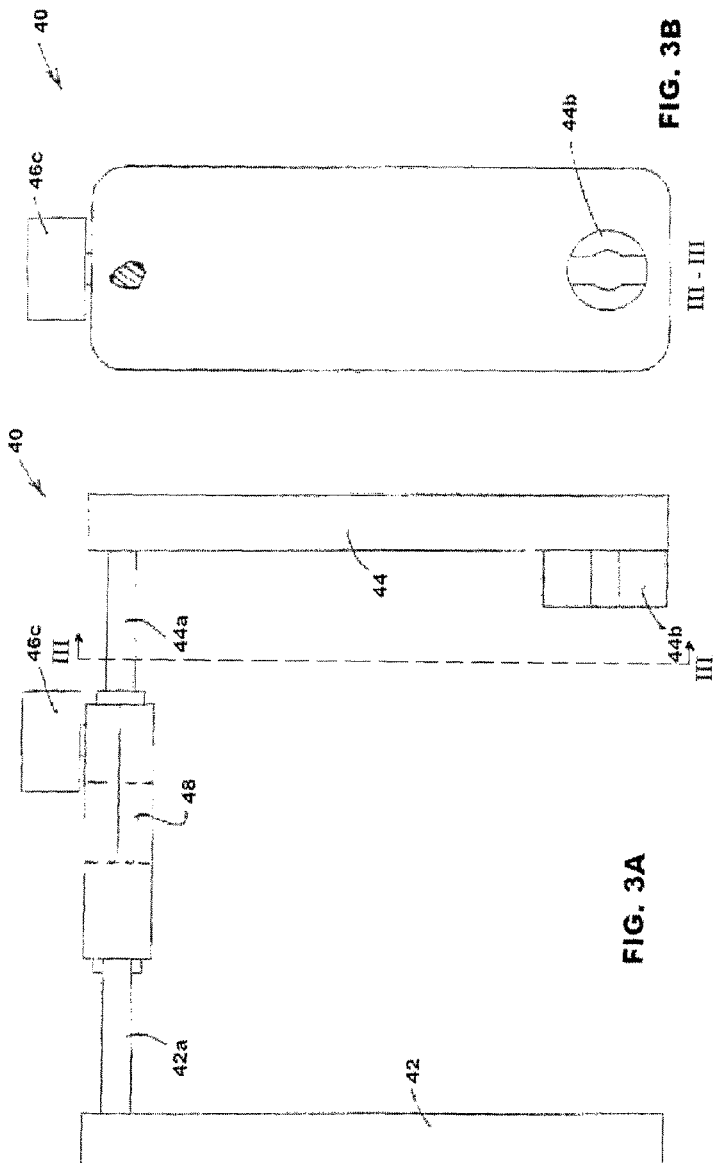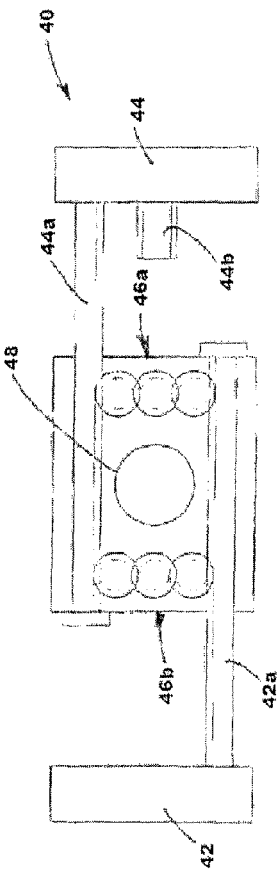

STABILIZER FOR A DENTAL IMPLANT SYSTEM AND DENTAL IMPLANT SYSTEM

CROSS-REFERENCE TO RELATED APPLICATIONS

This application is a non-provisional counterpart to and claims priority from U.S. Ser. No. 61/421,393 filed on Dec. 9, 2010, which is pending and which is hereby incorporated in its entirety by reference for all purposes.

BACKGROUND OF THE INVENTION

1. Field of the Invention

The invention relates to one or more stabilizers for a dental implant, a dental implant system including one or more stabilizers, and a method for implantation.

2. Discussion of the Related Art

When a patient has lost one or more teeth due to disease or age, dental implants may be installed in the affected location of the upper or lower jaw to hold a single tooth or in multiple locations to hold a dental bridge.

Implantation is made in the alveolar ridge of the patient. Since the alveolar ridge varies in depth, being higher at a patient's incisors and being lower from the canines to the molars, i.e., herein "reduced-depth locations," dental implants must also vary in the installation depth. Thus, in practice, dental manufacturers vary the implant-seated portion, which is the portion implanted in the bone and which is below the bottom of the patient's gum.

The implant seated portion typically consists of the thread portion, which retains the implant in the alveolar ridge and prevents dislocation, of dental implants. Dental implants that are used to replace incisors will have a longer implant-seated portion than dental implants used to replace canines, i.e., cuspids, pre-molars, or molars.

However, typical dental implants require certain anchorage depths when installed in reduced-depth locations. Such anchorage may be difficult to achieve when a patient's tooth roots or nerves interfere with the preferred location of the implant-seated portion. Oral surgeons and dentists try to remedy this by re-locating the implant-seated portion, angling the implant-seated portion, or using narrow-body dental implants. These may not satisfactorily resolve the problems.

Thus, what is needed is an implant system that may be effectively used in one or more reduced-depth locations.

SUMMARY OF THE INVENTION

These and other objectives are met by one or more embodiments of the present invention. Therein, in accordance with one or more embodiments of the present invention, a stabilizer for an implant system includes a manipulation portion for handling and locating the stabilizer relative to a bone and a main body for securing an implant, the main body including a general U-shape. The main body may further include a first and second leg portion and a manipulation channel, wherein each leg portion is divided into an upper and lower portion. The manipulation channel may include a distal end portion proximate to the manipulation portion, the end portion including a cross-section larger than a cross-section of the manipulation to permit a tool to expand inside the stabilizer to securely grasp the stabilizer.

The stabilizer may include a transverse channel for connecting the stabilizer and an implant, the transverse channel having an axis perpendicular to an axis of the manipulation channel. The manipulation portion includes a thread for engaging the stabilizer with a manipulation tool. The transverse channel includes a thread for engaging a thread of the implant.

In accordance with one or more embodiments of the present invention, an implant system includes an implant and a stabilizer. The stabilizer includes a manipulation portion for handling and locating the stabilizer and a main body having a manipulation channel and a transverse channel for connecting the stabilizer and an implant, the transverse channel having an axis perpendicular to an axis of the manipulation channel. The implant includes a first thread, the transverse channel includes a second thread for engaging the first thread. The first thread is made of a harder material than the second thread of the transverse channel for interlocking the implant and the stabilizer. The implant may also have a flush distal end.

The system may further include a jig fixture having a first arm and a second arm responsive to a manipulator, the first arm for engaging the manipulation portion, the second arm for engaging the manipulation channel.

The system may further include a drill unit for a hand drill having a first end portion having a reduced diameter relative to a diameter of a main portion of the drill unit, wherein the reduced diameter is smaller than an unthreaded diameter of the transverse channel.

A method for installing an implant includes the steps of:
(a) drilling a hole in a cross-ridge direction in a bone;
(b) inserting a stabilizer in the hole;
(c) locating an implant hole using a jig fixture attached to the stabilizer;
(d) drilling an implant hole;
(e) inserting an implant in the implant hole; and
(f) engaging the stabilizer with the implant.

BRIEF DESCRIPTION OF THE DRAWINGS

FIG. 1a is a top view of a stabilizer in accordance with one embodiment of the present invention.

FIG. 1b is an elevational view of the stabilizer of FIG. 1a.

FIG. 1c is a cross-sectional view of the stabilizer of FIG. 1a taken along line B-B.

FIG. 1d is a cross-sectional view of the stabilizer of FIG. 1a taken along line A-A.

FIG. 2b is a top view of the implant of FIG. 2a.

FIG. 3a is an elevation view of a guide in accordance with one or more embodiments of the present invention.

FIG. 3b is an elevation view of the guide of FIG. 3a taken perpendicular to FIG. 3a.

FIG. 3c is a bottom view of the guide of FIG. 3a.

DETAILED DESCRIPTION OF THE INVENTION

Figure 2B:
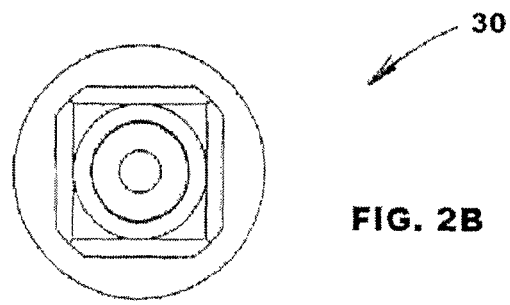

Reference will now be made in detail to several views of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, left, right, up, down, over, above, below, beneath, rear, and front may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

FIG. 1a is a top view of a stabilizer in accordance with one embodiment of the present invention. FIG. 1b is an elevational view of the stabilizer of FIG. 1a. FIG. 1c is a cross-sectional view of the stabilizer of FIG. 1a taken along line B-B. FIG. 1d is a cross-sectional view of the stabilizer of FIG. 1a taken along line A-A.

Figure 2A:
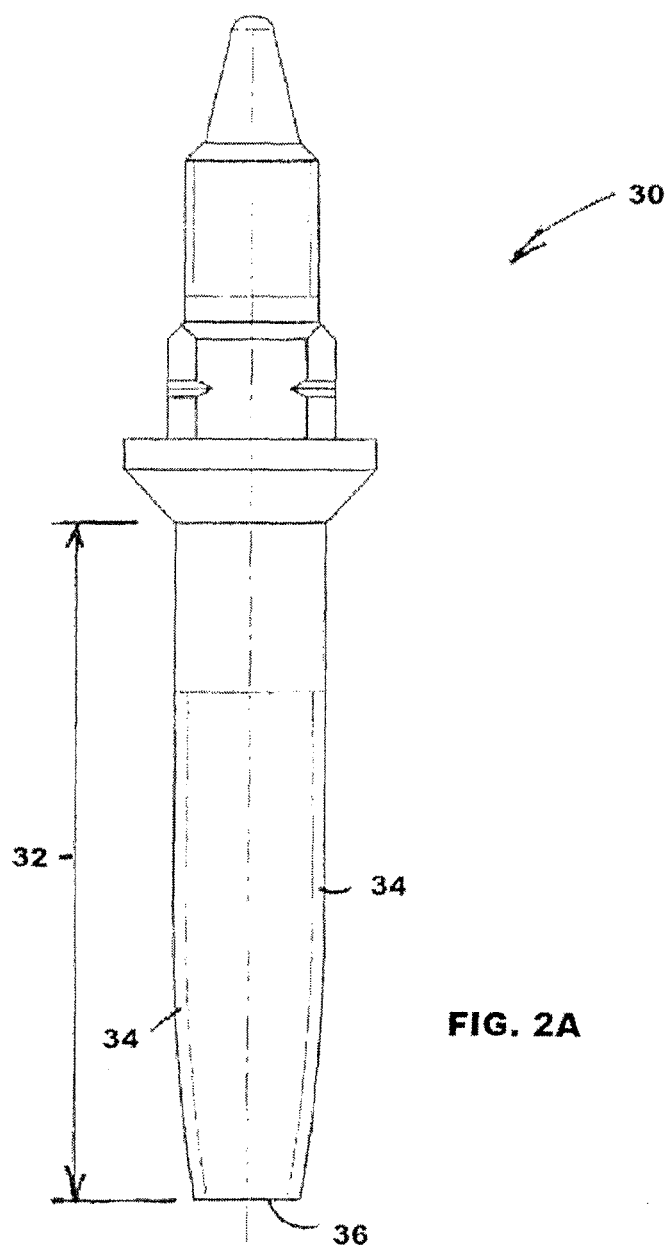
FIG. 2a is an elevational view of an implant in accordance with one or more embodiments of the present invention.

FIG. 2a is an elevational view of an implant in accordance with one or more embodiments of the present invention. FIG. 2b is a top view of the implant of FIG. 2a.

FIG. 3a is an elevation view of a guide in accordance with one or more embodiments of the present invention. FIG. 3b is an elevation view of the guide of FIG. 3a taken perpendicular to FIG. 3a. FIG. 3c is a bottom view of the guide of FIG. 3a.

Figure 4:
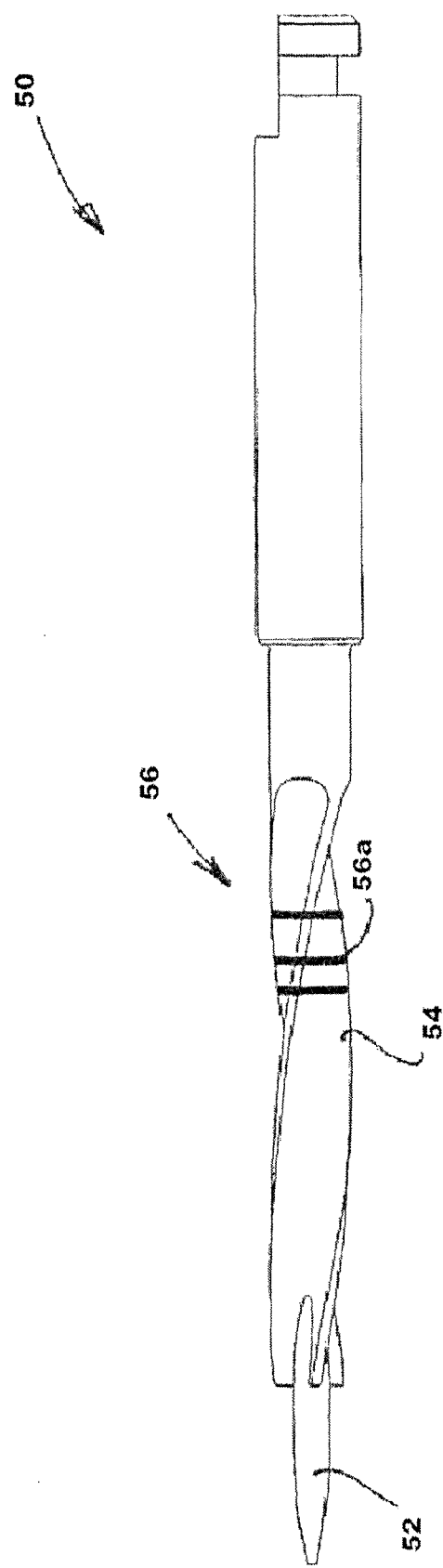
FIG. 4 is an elevation view of a drill unit in accordance with one or more embodiments of the present invention.

FIG. 4 is an elevation view of a drill unit in accordance with one or more embodiments of the present invention.

Figure 5A:
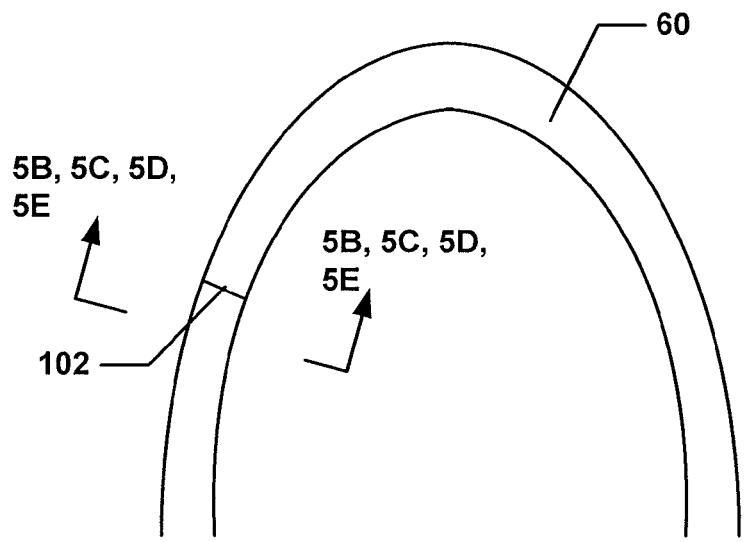
FIG. 5a is a top schematic view of an alveolar ridge in a lower jaw of a patient.
Figure 5B:
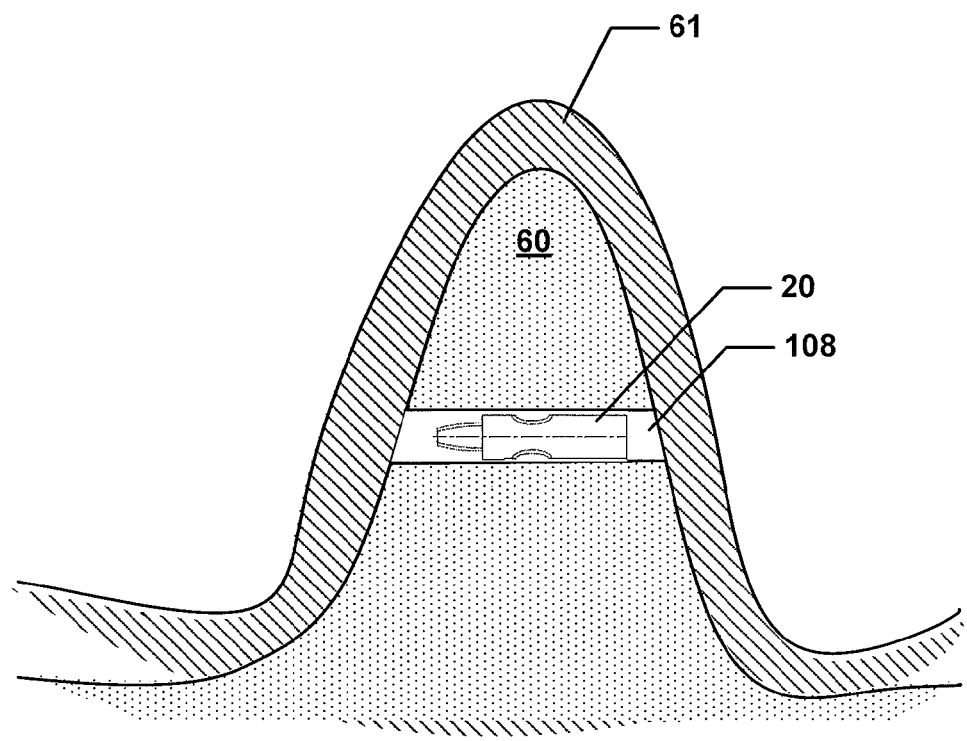
FIG. 5b is a cross-sectional view of the alveolar ridge of FIG. 5a with a stabilizer implanted.
Figure 5C:
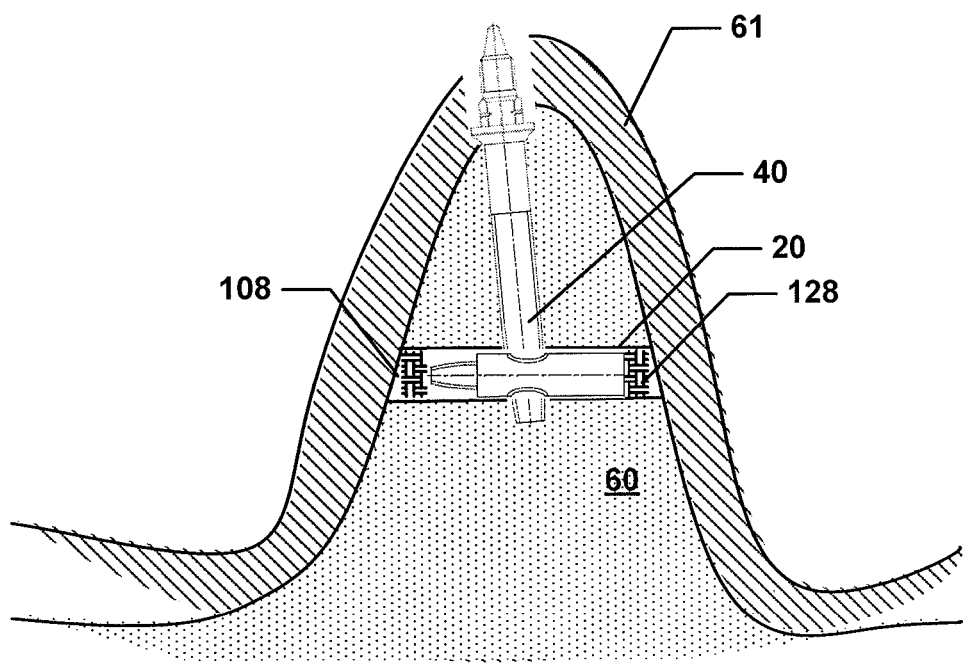
FIG. 5c is a cross-sectional view of the alveolar ridge of FIG. 5a with an implant engaged with the stabilizer.

FIG. 5a is a top schematic view of an alveolar ridge in a lower jaw of a patient. FIG. 5b is a cross-sectional view of the alveolar ridge of FIG. 5a with a stabilizer implanted. FIG. 5c is a cross-sectional view of the alveolar ridge of FIG. 5a with an implant engaged with the stabilizer.

In accordance with one or more embodiments of the present invention, a dental implant system 10 includes one or more the following: an implant stabilizer 20, an implant 30, a jig fixture 40, and a drill unit 50. System 10 may be effectively used in reduced-depth locations to avoid interference with existing tooth roots or nerves in the patient's alveolar ridge. System 10 may also be used in other locations as desired by an oral surgeon or dentist, i.e., "dental professional."

System 10 may also be suitably adapted by, for example, scaling it to a size suitable for use in bone implantation, such as replacements of all or a portion of the bones in the leg and/or arm of a human and/or animal.

Stabilizer 20 comprises a manipulation portion 22 for handling and locating stabilizer 20 precisely in an opening created in the patient's alveolar ridge and a main body 24 for securing implant 30 in the stabilizer. One or more threads 22a may be disposed over all or the entire outer surface of portion 22 to permit engagement with a manipulation tool.

Main body 24 comprises a general U-shape having an end portion 24a proximal to manipulation portion 22 and first and second leg portions 24b and 24c. Each leg portion is divided into an upper and lower portion by an alignment and manipulation channel 24d having a preferably circular cross-section. Channel 24d helps align stabilizer 20 in the correct position and after implantation permits bone to grow in channel 24d to further secure stabilizer 20. As can be seen in Figs. 1c and 1d, each first and second leg portions 24b and 24c is indented to form, in part, manipulation channel 24d. The indentations start at an end of first and second leg portions 24b and 24c that is distal from manipulation portion 22 and extend to a transverse channel 25.

Channel 24d may have a distal end portion 24e, which is proximate to manipulation portion 22. End portion 24e is larger in cross-section than the remainder of channel 24d and permits a tool to expand inside for securely holding stabilizer 20.

A transverse central channel 25 is formed having one or more threads 25a, preferably through the entire interior perimeter of channel 25, to engage one or more threads on implant 30 and to connect stabilizer 20 and implant 30 together. Channel 25 also preferably has indentations 25b for easy manipulation and for easier entry of implant 30. Therein, channel 25 has an axis that is perpendicular to an axis of the channel 24d.

Stabilizer 20 and its components may be dimensioned as shown and disclosed in U.S. Ser. No. 61/421,393, which is hereby incorporated in its entirety for all purposes, and specifically in sheets A, B, and C, therein. The corners of stabilizer 20 may be chamfered and/or rounded for patient comfort and ease of use by dental professionals.

Implant 30 may be any kind of suitable implant, such as those made and/or sold by Dentatus Ltd of New York, N.Y. Therein, implant 30 includes an implant-seated portion 32 and a one or more threads 34 that secure implant 30 in the alveolar ridge and in stabilizer 20 by engaging one or more threads 25a. Since implant 30 is secured at least in part or wholly by stabilizer 20, advantageously, the length of implant-seated portion 32 may be reduced over the length implant-seated portion of similar implants.

In accordance with one or more embodiments of the present invention, implant 30 may comprise a distal end 36 that is flush rather than pointed and/or peaked end advantageously avoiding further bone loss.

Figure 6A:
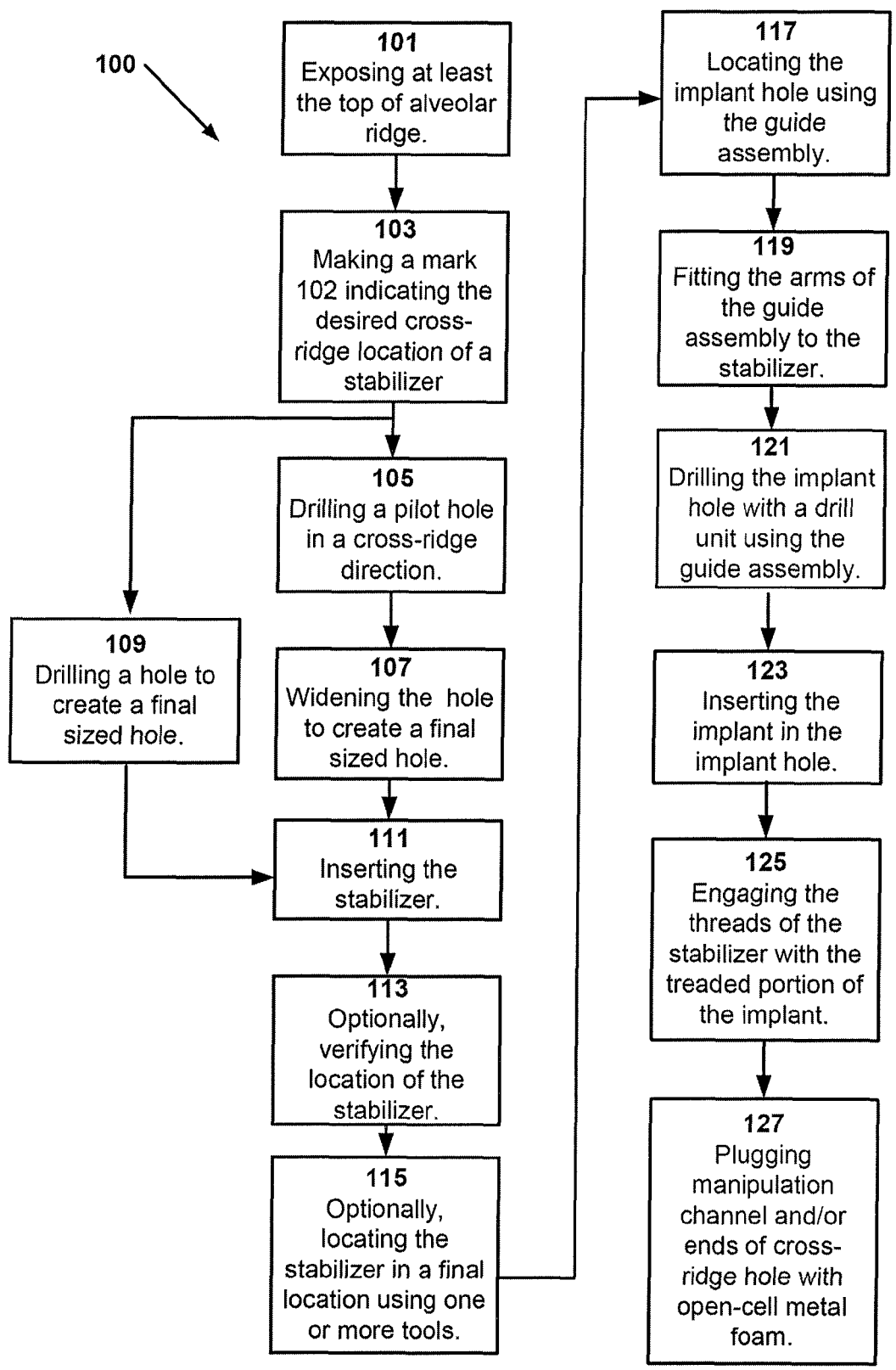
FIG. 6a is a flow diagram of an installation procedure using at least a stabilizer of the present invention in accordance with one or more embodiments of the present invention.

FIG. 6a is a flow diagram of an installation procedure using at least a stabilizer of the present invention in accordance with one or more embodiments of the present invention. In use, an installation procedure 100 for installing an implant, the installation procedure begins with a step 101 by exposing at least the top of the alveolar ridge of the patient by, for example, making a flap in the gums and laying the gum flap 61 back to expose the alveolar ridge 60. After consideration by the professional of the best position of implant 30, in a step 103, a mark 102 indicating the desired cross-ridge location of stabilizer 20 may be made using any suitable instrument such as a drill in the patient's alveolar ridge 60 as shown in FIG. 5a.

The cross-ridge location and/or direction may be transverse to the alveolar ridge or at an angle to the proximate longitudinal direction of the alveolar ridge and may have also have an inclination or declination with respect to a plane of the top of the alveolar ridge in the proximate area of the cross-ridge location. That is, the cross-ridge location and/or direction may be aligned as best determined by the dental professional.

Next, in a step 105, a pilot hole in the cross-ridge direction, preferably using mark 102, is drilled in the alveolar ridge using any suitable drill. The pilot hole may be made using a needle point drill and actually made by beginning through the cheek tissue of the patient. That is, the hole maybe made wherein the hole begins at the outside face of the patient. The needle point drill preferably is fine enough not to damage the tissue and may be made through the gum and into the alveolar ridge. The pilot hole may then exit through the alveolar ridge and extend through the lingual side of the gums.

In a step 107, a second drill may be used to widen the pilot hole to create final sized cross-ridge hole 108 suitably large enough, i.e., at least as large as the cross-section of the stabilizer, for installation of stabilizer 20. In the alternative, a step 109 single drill procedure, i.e., wherein step 105 is completed with a suitably sized drill, is used to create final sized cross-ridge hole 108 suitably large enough, i.e., at least as large as the cross-section of the stabilizer, for installation of stabilizer 20.

Instead of starting drilling for the cross-ridge hole through the patient's outside face, the dental professional may drill from the lingual side of the alveolar ridge and/or the outside tooth side using any suitable drill.

After the cross-ridge hole has been finished, in a step 111, the stabilizer is inserted so that channel 25 becomes accessible to an implant inserted from the top of the alveolar ridge as indicated in FIG. 5b. In a step 113, the location of stabilizer 20 may be verified using X rays or any other suitable means. In a step 115, if manipulation of stabilizer 20 is required, this may be achieved using a tool that is threaded or otherwise engaging manipulation portion 22 and/or channel 24d and/or end portion 24e.

Then, in a step 117, an implant hole for implant 30 is prepared by first locating the implant hole, which may be located using a jig fixture 40. Jig fixture 40 comprises a first end location arm 42 and a second end location arm 44 movable using gear assemblies 46a and 46b that are responsive to a manipulator 46c and that move struts 42a, 44a connected to arms 42, 44, respectively.

Arm 42 includes an opening (not shown) that receives a tip portion of manipulation portion 22 for correctly locating one end of the stabilizer 20 and arm 44 includes an end portion 44b that is received in channel 24d for correctly locating the other end of stabilizer 20. Therein, end portion 44b maybe configured to comprise a key that is fitted in a predetermined manner in channel 24d configured as a keyway. In the alternative, arm 44 includes an end portion 44b that receives a tip portion of manipulation portion 22 for correctly locating one end of the stabilizer 20 and arm 42 includes an end portion (not shown) that engages the other end of stabilizer 20.

When manipulator 46c is turned, gear assemblies 46a and 46b move arms 42 and 44 according to a predetermined ratio relative to each other. This permits arms 42 and 44 to be fitted onto the ends of stabilizer 20 in a step 119. By spacing arms 42, 44 using gear assemblies 46a, 46b, a guide hole 48 will align with channel 25.

Once arms 42 and 44 are fitted onto the ends of stabilizer 20, the dental professional may then have a guide for drilling the implant hole using the guide hole 48 of jig fixture 40 in a step 121. The implant hole may be drilled with any suitable drill.

In accordance with one or more embodiments of the present invention, step 121 may be performed but need not necessary be done so by a drill unit 50 used in a typical hand drill for making the implant hole. Drill unit 50 comprises a first end portion 52 having a reduced diameter relative to a diameter of a main portion 54. The diameter of end portion 52 is smaller than the diameter of channel 25 and/or the distance between the edges of threads 25a located along a diameter of the shaft, i.e., herein "the unthreaded diameter", to avoid damaging the shaft and/or threads, respectively. The diameter of main body portion 54 may correspond identically or be substantially similar to a diameter of implant-seated portion 32.

Base region 56 may have one or more marks 56a that indicate a target length relative to a tip of the drill unit for guiding the dental professional to the desired length of the hole and avoid damaging threads 25a and/or channel 25.

Implant 30 is then inserted into the implant hole in step 123 and advanced until one or more threads 34 engage one or more threads 25a of channel 25 in a step 125 as indicated in FIG. 5c. Therein, implant 30 may be made using a titanium allow, such as grade 5 titanium, that is harder than the material, such as a pure titanium, of the stabilizer. Thus, the nominal diameter of the implant-seated portion 32 and channel 25 of the stabilizer are selected such that the threads of each engage each other. If there is interference between the threads, the harder threads of implant 30 will damage the threads 25a of the stabilizer, but continue to permit insertion of the implant to its intended location. The damaged threads 25a will help interlock the threads.

In accordance with one or more embodiments of the present invention, after the installation is complete, in a step 127, preferably channel 24d and/or portions of hole 108 may be filled and/or plugged with one or more types of open-cell metal foam 128 as disclosed in non-patent literature magazine Orthetec, July/August 2011 at pages 26-28 and made preferably according to the developments of Fraunhofer Institute Center IZD in Dresden, Germany. The open cell metal foam may comprise titanium or an alloy such as a titanium grade 5 (ASTM) alloy having $Ti_6Al_4V$.

Figure 5D:
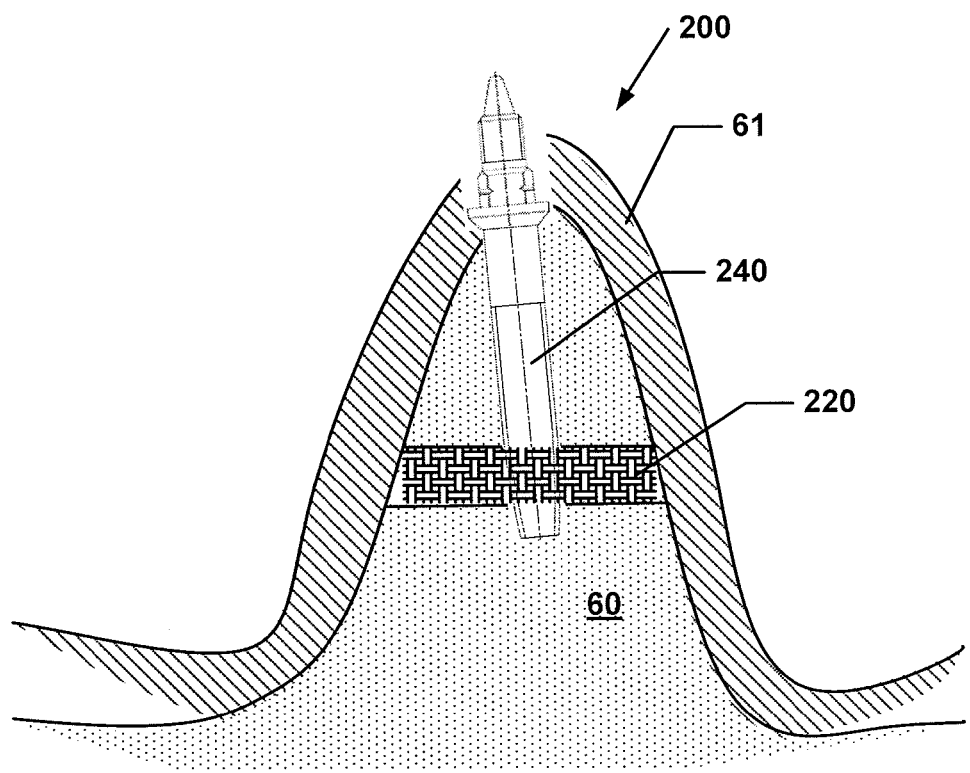
FIG. 5d is a cross-sectional view of the alveolar ridge with an implant engaged with a stabilizer comprising an open-cell metal foam.

In accordance with one or more embodiments of the present invention, FIG. 5d is a cross-sectional view of the alveolar ridge with an implant engaged with a stabilizer comprising an open-cell metal foam as described above. In accordance with one or more embodiments of the present invention, an implant system 200 comprises a stabilizer 220 comprising an open-cell metal foam as described above and an implant 240 configured to be substantially similar to implant 40. Implant 240 engages an intact section of the metal foam and due to a greater hardness and/or density will create a path, i.e., push the foam apart where necessary, and have the threads of implant 240 lock into the metal foam.

Therein, method 100 is performed by inserting in step 111 the stabilizer 220. Advantageously, the stabilizer 220 does not need to be located exactly since the implant lockingly engages with the metal foam. Thus, one or more steps 113, 115, 117, and 119 need not be performed. Then, steps 121 and 123 are performed, and step 125 is performed by having implant 240 engage an intact section of the metal foam and due to a greater hardness and/or density will create a path, i.e., push the foam apart where necessary, and have the threads of implant 240 lock into the metal foam. Step 127 need not be performed if the initial size of the foam selected for the stabilizer is suitably sized.

Figure 6B:
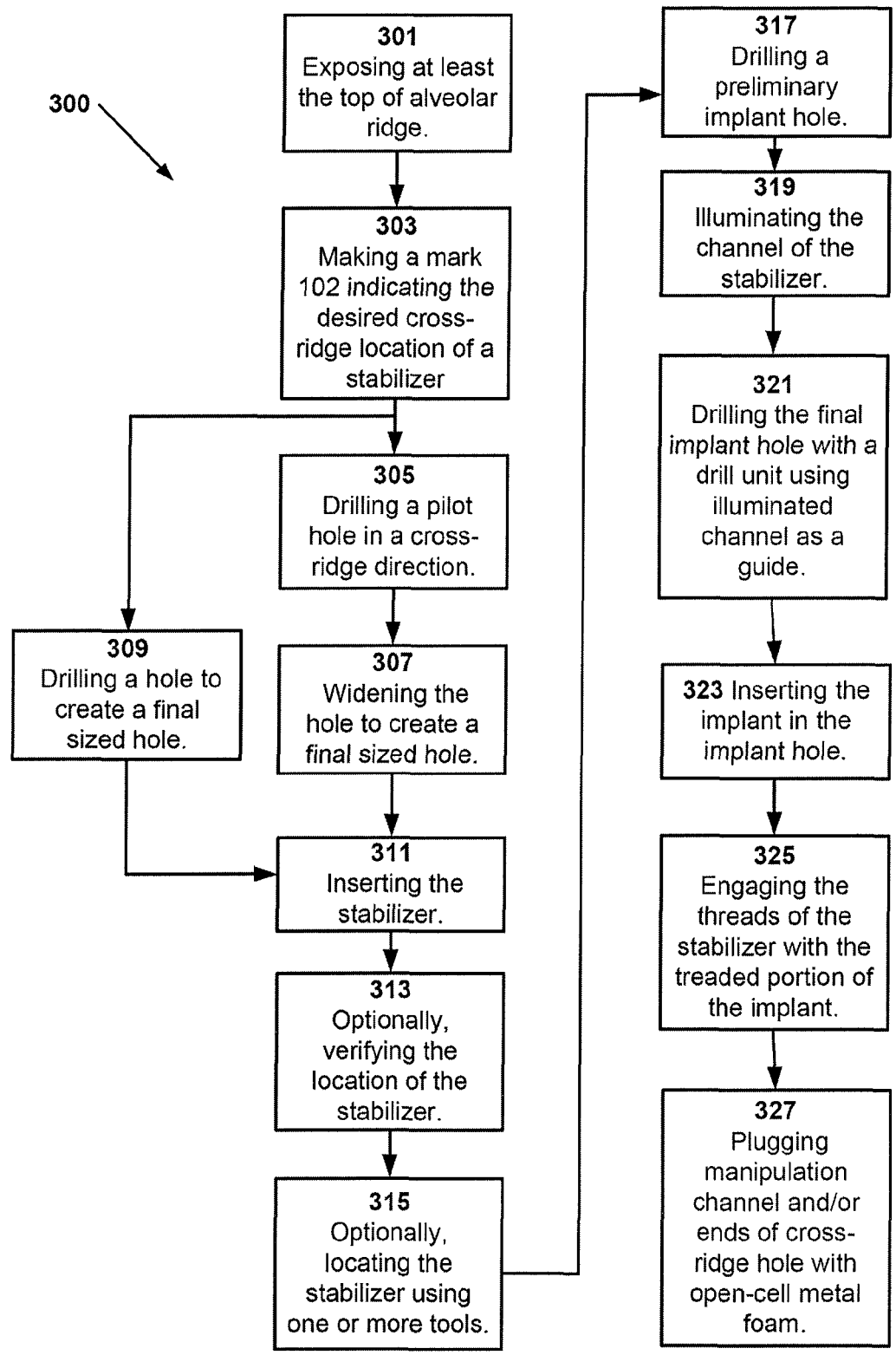
FIG. 6b is a flow diagram of an installation procedure using at least a stabilizer of the present invention in accordance with one or more other embodiments of the present invention.

FIG. 6b is a flow diagram of an installation procedure using at least a stabilizer of the present invention in accordance with one or more embodiments of the present invention. In accordance with one or more embodiments of the present invention, an installation procedure 300 for installing an implant includes the use of a light source.

The installation procedure begins with a step 301 by exposing at least the top of the alveolar ridge of the patient by, for example, making a flap in the gums and laying the gum flap 61 back to expose the alveolar ridge 60. After consideration by the professional of the best position of the implant, in a step 303, a mark 102 indicating the desired cross-ridge location of a stabilizer, such as stabilizer 20, may be made using any suitable instrument such as a drill in the patient's alveolar ridge 60 as shown in FIG. 5a.

The cross-ridge location and/or direction may be transverse to the alveolar ridge or at an angle to the proximate longitudinal direction of the alveolar ridge and may have also have an inclination or declination with respect to a plane of the top of the alveolar ridge in the proximate area of the cross-ridge location. That is, the cross-ridge location and/or direction may be aligned as best determined by the dental professional.

Next, in a step 305, a pilot hole is made in the cross-ridge direction, preferably using mark 102, is drilled in the alveolar ridge using any suitable drill. The pilot hole may be made using a needle point drill and actually made by beginning through the cheek tissue of the patient. That is, the hole maybe made wherein the hole begins at the outside face of the patient. The needle point drill preferably is fine enough not to damage the tissue and may be made through the gum and into the alveolar ridge. The pilot hole may then exit through the alveolar ridge and extend through the lingual side of the gums.

In a step 307, a second drill may be used to widen the pilot hole to create final sized cross-ridge hole 308 suitably large enough, i.e., at least as large as the cross-section of the stabilizer, for installation of a stabilizer 320, such as a stabilizer substantially similar to stabilizer 20. In the alternative, a step 309 single drill procedure, i.e., wherein step 305 is completed with a suitably sized drill, is used to create final sized cross-ridge hole 308 suitably large enough, i.e., at least as large as the cross-section of the stabilizer, for installation of the stabilizer.

Instead of starting drilling for the cross-ridge hole through the patient's outside face, the dental professional may drill from the lingual side of the alveolar ridge and/or the outside tooth side using any suitable drill.

After the cross-ridge hole has been finished, in a step 311, stabilizer 320 is inserted so that a channel 25, such as one substantially similar to channel 25 of stabilizer 20, becomes accessible to an implant inserted from the top of the alveolar ridge as indicated in FIG. 5b. In a step 313, the location of stabilizer 320 is preliminarily verified. In a step 315, if manipulation of stabilizer 320 is required, this may be achieved using a tool that is threaded or otherwise engaging manipulation portion 22 and/or channel 24d and/or end portion 24e.

Then, in a step 317, a preliminary implant hole 318 for implant 30 is prepared by first drilling a pilot hole with preferably a needlepoint drill.

Figure 5E:
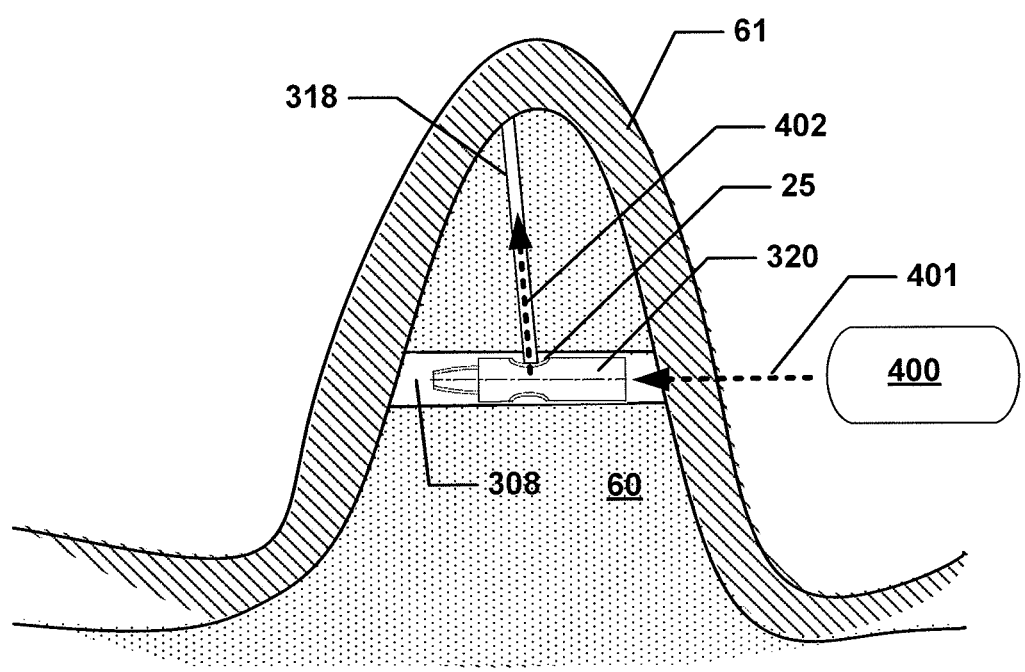
FIG. 5e is a cross-sectional view of the alveolar ridge of FIG. 5a with a light source illuminating a channel of a stabilizer in a preliminary implant hole.

FIG. 5e is a cross-sectional view of the alveolar ridge of FIG. 5a with a light source illuminating a channel of a stabilizer in a preliminary implant hole. In a step 319, a light source 400 is operatively placed to illuminate channel 24d. A light curable post (not shown), such as one taught in U.S. Pat. No. 5,326,263, which is hereby incorporated in its entirety by reference for all purposes, may have be inserted in channel 24d to conduct ambient light or conduct light 401 from light source 400 and illuminate one or more portions of channel 25 and/or the stabilizer walls defining channel 25. Light source 400 may be any suitable light source and may preferably be a laser.

In accordance with one or more embodiments of the present invention, light source 400 is a laser and distal end portion 24e is configured to reflect the laser such that one or more portions of the stabilizer walls defining channel 25 are illuminated and/or a temporary or permanent target disposed in channel 25 and/or the stabilizer walls defining channel 25 are illuminated.

In accordance with one or more embodiments of the present invention, light source 400 or ambient light illuminates the light curable post to illuminate one or more portions of channel 25 and/or the stabilizer walls defining channel 25.

In a step 321, the position of the stabilizer is adjusted using the tool that is threaded or otherwise engaging manipulation portion 22 and/or channel 24d and/or end portion 24e so that channel 25 can be determined through the preliminary implant hole using the illumination 402 as seen through the preliminary implant hole as a guide. If necessary, the stabilizer is moved and a final implant hole is made. Advantageously, this eliminates the use of jig fixture 40.

In accordance with one or more embodiments of the present invention, step 321 may be performed but need not necessary be done so by drill unit 50 used in a typical hand drill for making the implant hole. Step 321 is performed at least partially as described with respect to step 121.

Implant 30 is then inserted into the implant hole in step 323 and advanced until one or more threads 34 engage one or more threads 25a of channel 25 in a step 325 as indicated in FIG. 5c. Therein, implant 30 may be made using a titanium allow, such as grade 5 titanium, that is harder than the material, such as a pure titanium, of the stabilizer. Thus, the nominal diameter of the implant-seated portion 32 and channel 25 of the stabilizer are selected such that the threads of each engage each other. If there is interference between the threads, the harder threads of implant 30 will damage the threads 25a of the stabilizer, but continue to permit insertion of the implant to its intended location. The damaged threads 25a will help interlock the threads.

In accordance with one or more embodiments of the present invention, after the installation is complete, in a step 327, preferably channel 24d and/or portions of hole 308 may be filled and/or plugged with one or more types of open-cell metal foam 128 as disclosed in non-patent literature magazine Orthetec, July/August 2011 at pages 26-28 and made preferably according to the developments of Fraunhofer Institute Center IZD in Dresden, Germany. The open cell metal foam may comprise titanium or an alloy such as a titanium grade 5 (ASTM) alloy having $Ti_6Al_4V$.

While the invention has been described in conjunction with specific embodiments, it is to be understood that many alternatives, modifications, and variations will be apparent to those skilled in the art in light of the foregoing description.

What is claimed is:

1. A stabilizer for a dental implant system, the stabilizer comprising:
    a first end and a second end opposite the first end;
    a manipulation portion disposed on the first end, the manipulation portion for handling and locating the stabilizer relative to a bone; and
    a main body proximal to the manipulation portion for securing a dental implant, the main body comprising
        a general U shape,
        a manipulation channel having a longitudinal axis,
        a first leg and a second leg not directly connected to the first leg, each leg extending along the longitudinal axis,
        a transverse channel for connecting the stabilizer and the dental implant, the transverse channel and the manipulation channel intersecting each other perpendicularly in the main body;
    wherein each leg is indented along the longitudinal axis to partially form the manipulation channel from the second end to the transverse channel.

2. The stabilizer of claim 1, further comprising an end portion, wherein the end portion is proximate to the manipulation portion, the end portion comprising a cross section larger than a cross-section of the manipulation channel to permit a tool to expand inside the stabilizer to securely grasp the stabilizer.

3. The stabilizer of claim 1, wherein the manipulation portion comprises a thread for engaging the stabilizer with a manipulation tool.

4. The stabilizer of claim 1, wherein each leg portion comprises a thinned section at the transverse channel.

5. The stabilizer of claim 4, wherein the transverse channel comprises a first thread for engaging a second thread of the dental implant.

6. The stabilizer of claim 1, wherein the manipulation portion comprises a substantially frustoconical shape.

7. The stabilizer of claim 1, wherein the U-shape of the main body portion is open at the second end.

8. The stabilizer of claim 1, wherein either the transverse channel or the manipulation channel comprises a circular shape in cross-section.

9. The stabilizer of claim 1, wherein the main body member comprises a substantially circular cross-section.

10. The stabilizer of claim 1,
wherein the first leg and the second leg are spaced apart from each other; and
wherein the manipulation channel does not extend into the manipulation portion.

11. A dental implant system comprising:
a dental implant and a stabilizer,
the stabilizer comprising
a first end and a second end opposite the first end;
a manipulation portion disposed on the first end, the manipulation portion for handling and locating the stabilizer relative to a bone;
a main body proximal to the manipulation portion for securing the e dental implant, the main body comprising
a manipulation channel having a longitudinal axis,
a first leg and a second leg not directly connected to the first leg, each leg extending along the longitudinal axis,
a transverse channel for connecting the stabilizer and the dental implant, the transverse channel and the manipulation channel intersecting each other perpendicularly in the main body;
wherein each leg is indented along the longitudinal axis to partially form the manipulation channel from the second end to the transverse channel.

12. The dental implant system of claim 11, wherein the dental implant comprises a first thread, the transverse channel comprises a second thread for engaging the first thread.

13. The dental implant system of claim 12, wherein the first thread comprises a harder material than the second thread of the transverse channel for interlocking the dental implant and the stabilizer.

14. The dental implant system of claim 11, wherein the dental implant comprises a flush distal end.

15. The dental implant system of claim 11, further comprising a jig fixture, the jig fixture comprising a first arm and a second arm responsive to a manipulator, the first arm for engaging the manipulation portion, the second arm for engaging the manipulation channel.

16. The dental implant system of claim 15, further comprising a drill unit for a hand drill, the drill unit comprising a first end portion having a reduced diameter relative to a diameter of a main portion of the drill unit, wherein the reduced diameter is smaller than an unthreaded diameter of the transverse channel.

17. The dental implant system of claim 11, further comprising a drill unit for a hand drill, the drill unit comprising a first end portion having a reduced diameter relative to a diameter of a main portion of the drill unit, wherein the reduced diameter is smaller than an unthreaded diameter of the transverse channel.

18. The dental implant system of claim 11, wherein either the transverse channel or the manipulation channel comprises a circular shape in cross-section.

19. The dental implant system of claim 11, wherein the main body member comprises a substantially circular cross-section.

20. The dental implant system of claim 11,
wherein the first leg and the second leg are spaced apart from each other and
wherein the manipulation channel does not extend into the manipulation portion.

21. A stabilizer for a dental implant system, the stabilizer comprising:
a first end and a second end opposite the first end;
a manipulation portion disposed on the first end, the manipulation portion for handling and locating the stabilizer relative to a bone; and
a main body proximal to the manipulation portion for securing a dental implant, the main body comprising a general U-shape, the main body comprising
a manipulation channel having a longitudinal axis,
a first leg and a second leg not directly connected to the first leg, each leg extending along the longitudinal axis; and
a transverse channel for connecting the stabilizer and the dental implant, the transverse channel being larger in cross-section than the manipulation channel, the transverse channel and the manipulation channel intersecting each other perpendicularly in the main body portion;
wherein the manipulation channel does not extend into the manipulation portion;
wherein the main body is indented along the longitudinal axis to partially form the manipulation channel from the second end to the transverse channel.

* * * * *